(12) United States Patent
Kojima

(10) Patent No.: US 8,857,734 B2
(45) Date of Patent: Oct. 14, 2014

(54) FLUID INJECTION DEVICE

(75) Inventor: Hideki Kojima, Matsumoto (JP)

(73) Assignee: Seiko Epson Corporation, Tokyo (JP)

(*) Notice: Subject to any disclaimer, the term of this patent is extended or adjusted under 35 U.S.C. 154(b) by 354 days.

(21) Appl. No.: 13/039,042

(22) Filed: Mar. 2, 2011

(65) Prior Publication Data

US 2011/0215170 A1    Sep. 8, 2011

(30) Foreign Application Priority Data

Mar. 3, 2010   (JP) ................. 2010-046299

(51) Int. Cl.
    *B05B 1/08*        (2006.01)
    *A61B 17/3203*     (2006.01)
(52) U.S. Cl.
    CPC ............ *B05B 1/08* (2013.01); *A61B 17/3203* (2013.01)
    USPC ........................ 239/102.1; 239/344
(58) Field of Classification Search
    CPC .... B05B 17/06; B05B 17/0669; B05B 17/063
    USPC ........ 239/102.1, 102.2, 589.1, 337, 344, 354, 239/361
    See application file for complete search history.

(56) References Cited

U.S. PATENT DOCUMENTS

| | | | | |
|---|---|---|---|---|
| 6,845,759 | B2 * | 1/2005 | Ohnishi et al. | 123/478 |
| 6,921,020 | B2 * | 7/2005 | Ivri | 239/4 |
| 7,901,374 | B2 * | 3/2011 | Seto et al. | 604/48 |
| 2003/0071139 | A1 * | 4/2003 | Ohnishi et al. | 239/102.2 |
| 2008/0086077 | A1 | 4/2008 | Seto et al. | |
| 2009/0065065 | A1 * | 3/2009 | Sand | 137/3 |
| 2011/0089256 | A1 | 4/2011 | Kojima | |

FOREIGN PATENT DOCUMENTS

| | | |
|---|---|---|
| JP | 01-313047 | 12/1989 |
| JP | 06-090957 | 4/1994 |
| JP | 2008-082202 | 4/2008 |
| JP | 2011-087918 | 5/2011 |
| WO | 2009-125387 | 10/2009 |

* cited by examiner

*Primary Examiner* — Davis Hwu
(74) *Attorney, Agent, or Firm* — Workman Nydegger

(57) ABSTRACT

A fluid injection device includes: a pulse generator which converts fluid into pulse flow; a suction pipe projecting from the pulse generator; an injection pipe which is eccentrically inserted into the suction pipe such that the outer circumferential surface of the injection pipe contacts the inner circumferential surface of the suction pipe, and has an injection opening communicating with the pulse generator; and a suction channel and a suction opening formed between the inner circumferential surface of the suction pipe and the outer circumferential surface of the injection pipe, wherein the injection pipe is fixed to the inner circumferential surface of the suction pipe in the vicinity of the injection opening.

4 Claims, 4 Drawing Sheets

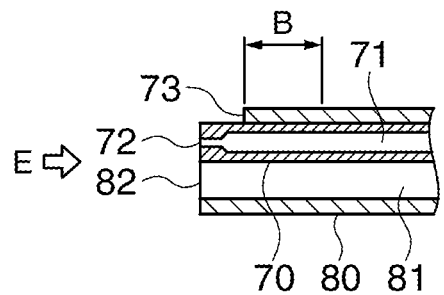
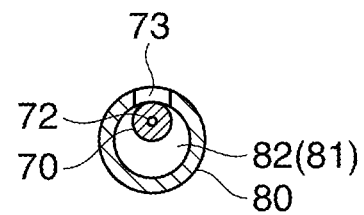
FIG. 9A  FIG. 9B
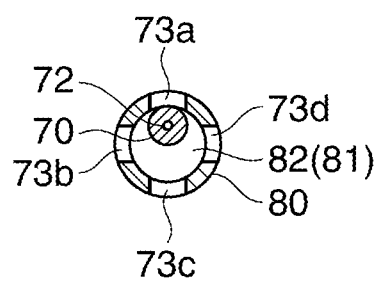
FIG. 10

FLUID INJECTION DEVICE

This application claims priority to Japanese Patent Application No. 2010-046299, filed on Mar. 3, 2010, the entirety of which is hereby incorporated by reference.

BACKGROUND

1. Technical Field

The present invention relates to a fluid injection device including an injection pipe and a suction pipe.

2. Related Art

A method for excising, incising, and crushing a living tissue by using a fluid injection device has preferable characteristics as a surgical instrument such as capabilities of preventing heat damage and preserving blood vessels and other capillary tissues. When an operation is performed using the fluid injection device, injected liquid, excised tissues or the like which remains on the portion of surgery becomes an obstacle for securing vision in some cases. As a technology for overcoming this problem, such a fluid injection device further including a suction pipe capable of removing liquid or excised tissues by suction is known.

As an example of this type of fluid injection device, a device which has an injection pipe for injecting high-pressure fluid as a pipe disposed within a suction channel of a suction pipe in such a position as to be concentric with the suction channel has been proposed (see JP-A-1-313047).

Another example of the fluid injection device currently proposed includes an injection pipe for injecting high-pressure fluid as a pipe inserted eccentrically with respect to the inner circumferential surface of a suction pipe (see JP-A-6-90957).

A further example of the fluid injection device sharply changes the volume of a fluid chamber by using a volume varying unit to convert fluid into pulse flow and inject the pulse flow through an injection opening as pulses at high speed (see JP-A-2008-82202).

According to the technology disclosed in JP-A-1-313047, the inner circumferential surface of the suction pipe and the outer circumferential surface of the injection pipe are concentrically disposed. Thus, the size of the suction channel at a suction opening (the length of the clearance between the inner circumferential surface of the suction pipe and the outer circumferential surface of the injection pipe) becomes half of the difference between the inside diameter of the suction pipe and the outside diameter of the injection pipe. In this case, it is difficult to remote excised tissues larger than the size of the suction channel at the suction opening by suction. When the diameter of the suction pipe is increased to secure the sufficient size of the suction channel, the vision for surgery is narrowed.

According to the technology disclosed in JP-A-6-90957, the injection pipe is inserted eccentrically to the inner circumferential surface of the suction pipe. In this case, the size of the suction channel corresponds to the difference between the inside diameter of the suction pipe and the outside diameter of the injection pipe, and thus becomes larger than the size of the suction channel in the concentric structure shown in JP-A-1-313047 when the suction pipe and the injection pipe have the same diameters as those in the concentric structure. However, there is a possibility that vibration is generated at the top end of the injection pipe, that is, in the vicinity of the injection opening at the time of injection of high-pressure fluid. In this case, injection of fluid toward the target surgery portion becomes difficult.

Moreover, according to the structure which inserts the injection pipe eccentrically to the suction pipe as the structure shown in JP-A-6-90957, the position of the injection opening cannot be directly recognized by visual check. Thus, injection of fluid to the accurate position of the target surgery portion is difficult.

According to the fluid injection device disclosed in JP-A-2008-82202, excision can be achieved by using a smaller amount of fluid than the amount of high-pressure fluid injected as continuous streams used by the methods shown in JP-A-1-313047 and in JP-A-6-90957. In case of the structure disclosed in JP-A-2008-82202, however, there is a case in which a suction pipe is required for improvement of visual recognizability of the surgery portion or for removal of excised tissues by suction. In this case, the injection pipe can be inserted eccentrically to the inner circumferential surface of the suction pipe for increasing the size of the suction channel as in the structure shown in JP-A-6-90957. However, when fluid is injected as pulses in this structure, it is expected that vibration of the injection pipe becomes larger than vibration generated by continuous flow injection.

When vibration is generated on the injection pipe, abnormal noise is produced by contact between the injection pipe and the suction pipe. Moreover, when the suction pipe is resonated by vibration generated at the top end of the injection pipe (injection opening), injection of fluid toward the surgery portion becomes difficult.

SUMMARY

An advantage of some aspects of the invention is to provide a technology capable of solving at least a part of the problems described above and the invention can be implemented as the following forms or application examples.

APPLICATION EXAMPLE 1

This application example of the invention is directed to a fluid injection device which includes: a pulse generator which converts fluid into pulse flow; a suction pipe projecting from the pulse generator; an injection pipe which is eccentrically inserted into the suction pipe such that the outer circumferential surface of the injection pipe contacts the inner circumferential surface of the suction pipe, and has an injection opening communicating with the pulse generator; and a suction channel and a suction opening formed between the inner circumferential surface of the suction pipe and the outer circumferential surface of the injection pipe. In this case, the injection pipe is fixed to the inner circumferential surface of the suction pipe in the vicinity of the injection opening.

According to this application example, the injection pipe is eccentrically inserted into the suction pipe. In this case, the size of the suction channel corresponds to the difference between the inside diameter of the suction pipe and the outside diameter of the injection pipe. When the inside diameter of the suction pipe and the outside diameter of the injection pipe are d1 and d2, respectively, the size of the suction channel (length of clearance) is expressed as d1−d2. On the other hand, according to a structure which concentrically disposes the suction pipe and the injection pipe, the size of the suction channel corresponds to (d1−d2)/2. In this case, the size of the suction channel in the eccentric structure becomes larger than the size of the suction channel in the concentric structure. Thus, larger excised tissues can be sucked in the structure in which the injection pipe and the suction pipe are eccentrically disposed than in the structure in which the injection pipe and the suction pipe are concentrically disposed. In addition, the removal amount of injected drainage increases, providing preferable vision for surgery.

According to this structure, the injection pipe is fixed to the inner circumferential surface of the suction pipe in the vicinity of the injection opening. Thus, abnormal noise produced by contact between the injection pipe and the suction pipe caused by vibration at the top end of the injection pipe is prevented by reduction of the vibration thereat. Moreover, movement of the top end of the injection pipe (injection opening) caused by the vibration thereat and resonance of the suction pipe generated by the vibration can be both prevented. Thus, fluid can be accurately injected toward the surgery portion.

APPLICATION EXAMPLE 2

This application example of the invention is directed to the fluid injection device of the above application example, wherein a mark indicating the position of the injection opening is provided on the suction pipe in the vicinity of the suction opening.

According to the structure which eccentrically inserts the injection pipe into the suction pipe, an operator can recognize the position of the injection opening based on the mark indicating the position of the injection opening. Thus, fluid can be accurately injected toward the surgery portion.

APPLICATION EXAMPLE 3

This application example of the invention is directed to the fluid injection device of the above application example, wherein the mark is a notch formed in such a position as to overlap with the periphery of the suction opening, or a through hole opened in the vicinity of the suction opening.

The mark may be a seal or the like which indicates the position of the injection opening provided in the vicinity of the suction opening. When a notch as the mark is formed in such a position as to overlap with the periphery of the suction opening, the notch not only allows recognition of the position of the injection opening but also increases the size of the suction opening by the amount corresponding to the notch.

When the mark is constituted by a through hole, excised tissues on the side surface as well as excised tissues at the top end can be removed by suction.

BRIEF DESCRIPTION OF THE DRAWINGS

The invention will be described with reference to the accompanying drawings, wherein like numbers reference like elements.

FIGS. 3A and 3B are cross-sectional views showing cross sections taken along a line A-A in FIG. 2, wherein: FIG. 3A illustrates the first example; and FIG. 3B illustrates a related art.

FIGS. 9A and 9B show top ends of an injection pipe and a suction pipe according to a seventh example, wherein: FIG. 9A is a cross-sectional view; and FIG. 9B is a front view as viewed from the top ends (in the direction indicated by an arrow E).

FIG. 10 is a front view illustrating a top end of a suction pipe according to an eighth example.

DESCRIPTION OF EXEMPLARY EMBODIMENT

An exemplary embodiment according to the invention is hereinafter described with reference to the drawings.

The figures referred to in this embodiment are shown only as schematics the reduction scales of which for components and parts in the vertical and horizontal directions are different from the actual scales for convenience of easy understanding of the figures.

First Embodiment

Figure 1:
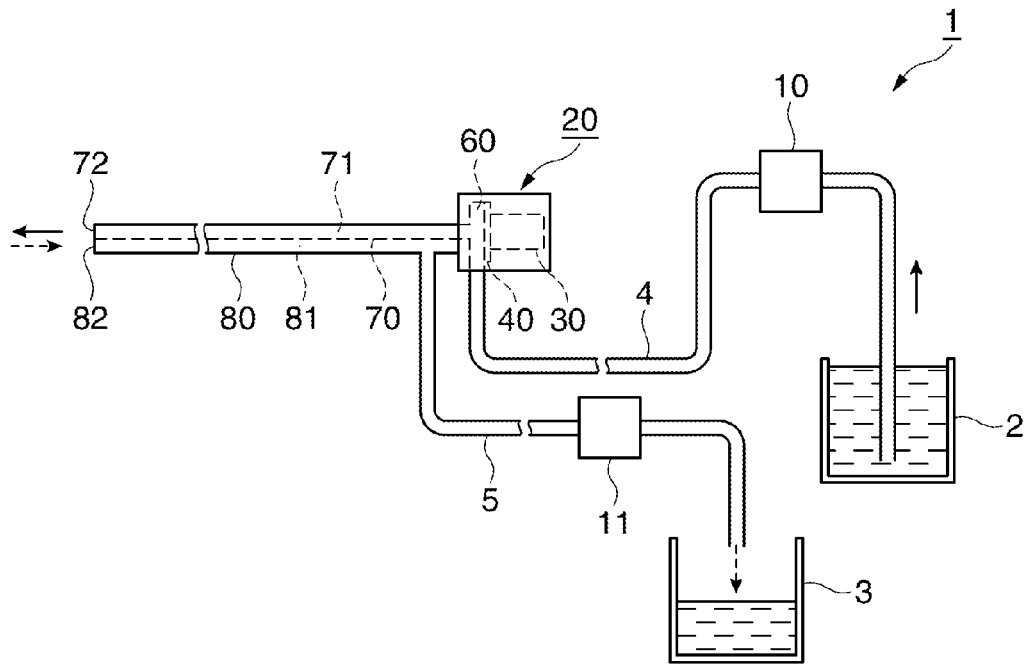
FIG. 1 illustrates the structure of a fluid injection device as a surgical instrument according to a first embodiment.

FIG. 1 illustrates the structure of a fluid injection device as a surgical instrument according to a first embodiment. Thus, fluid used in this embodiment described herein is constituted by physiological salt water. As illustrated in FIG. 1, a fluid injection device 1 includes a fluid supply container 2 for containing fluid, a supply pump 10 as a fluid supply unit, a pulse generator 20 for converting fluid supplied from the supply pump 10 into pulse flow (hereinafter referred to as pulse flow as well), an injection pipe 70 communicating with the pulse generator 20, a suction pipe 80 projecting from the pulse generator 20, a suction pump 11 as a suction unit, and a drainage container 3 for containing sucked drainage and excised tissues. The pulse generator 20, the supply pump 10, and the fluid supply container 2 are connected by a fluid supply tube 4. The suction pipe 80, the suction pump 11, and the drainage container 3 are connected by a suction tube 5.

The pulse generator for generating pulse flow may be operated by various systems such as a piezoelectric system including a piezoelectric element, and a bubble jet (trademark) system as long as the systems can convert fluid into pulse flow and inject the pulse flow as pulses. In the following explanation, a pulse generator operated by the piezoelectric system is discussed as an example.

The injection pipe 70 has an injection channel 71 communicating with a fluid chamber 60 formed within the pulse generator 20. An injection opening 72 having a narrowed flow channel is opened at the top end of the injection pipe 70.

The injection pipe 70 is eccentrically inserted into the suction pipe 80 such that the outer circumferential surface of the injection pipe 70 contacts the inner circumferential surface of the suction pipe 80. The injection pipe 70 is fixed to the inner circumferential surface of the suction pipe 80 in the vicinity of the injection opening 72 by bonding or other fixing methods. The clearance formed between the inner circumferential surface of the suction pipe 80 and the outer circumferential surface of the injection pipe 70 corresponds to a suction channel 81 and a suction opening 82. The injection pipe 70 is rigid enough to avoid deformation during injection of fluid. It is preferable that the suction pipe 80 is more rigid than the injection pipe 70.

The flow of fluid within the fluid injection device 1 constructed as above is now briefly explained. Fluid contained in the fluid supply container 2 is sucked by the supply pump 10, and supplied through the fluid supply tube 4 toward the pulse generator 20 at a constant pressure. The pulse generator 20 has the fluid chamber 60, a piezoelectric element 30 as a volume varying unit for varying the volume of the fluid chamber 60, and a diaphragm 40. The pulse generator 20 generates pulse flow within the fluid chamber 60 by driving the piezoelectric element 30, and injects the fluid having passed through the injection channel 71 as pulses from the injection opening 72 at high speed.

While the operation of the pulse generator 20 is stopping, that is, while the volume of the fluid chamber 60 is not being changed, the fluid supplied from the supply pump 10 at the constant pressure passes through the fluid chamber 60 and goes out of the injection opening 72 as continuous streams for injection.

The pulse flow herein refers to flow of fluid which has a constant flow direction but has a flow amount or a flow speed varying periodically or irregularly. The pulse flow includes intermittent flow where fluid repeats a cycle of flow and stop. However, the pulse flow may be flow other than the intermittent flow as long as the flow amount or the flow speed of fluid changes periodically or irregularly.

Similarly, injection of fluid as pulses refers to injection of fluid whose flow amount or moving speed varies periodically or irregularly. The injection as pulses includes intermittent injection which repeats a cycle of injection and non-injection of fluid, for example. However, the injection as pulses may be injection other than the intermittent injection as long as the flow amount or the moving speed of fluid to be injected changes periodically or irregularly.

The method of suction is now explained. The fluid injected from the injection opening 72 remains on the surgery portion as drainage. In addition, excised tissues exist on the surgery portion. These drainage and excised tissues are sucked by the suction pump 11, and conveyed from the suction opening 82 through the suction channel 81 and the suction tube 5 into the drainage container 3. The drive of the suction pump 11 may be interlocked with the drive of the pulse generator 20, or may be periodical intermittent drive.

There are a plurality of shapes and structures considered as suitable for those of the injection pipe 70 and the suction pipe 80. These shapes and structures are herein discussed as specific examples while referring to the respective drawings.

FIRST EXAMPLE

A first example is now described.

Figure 2:
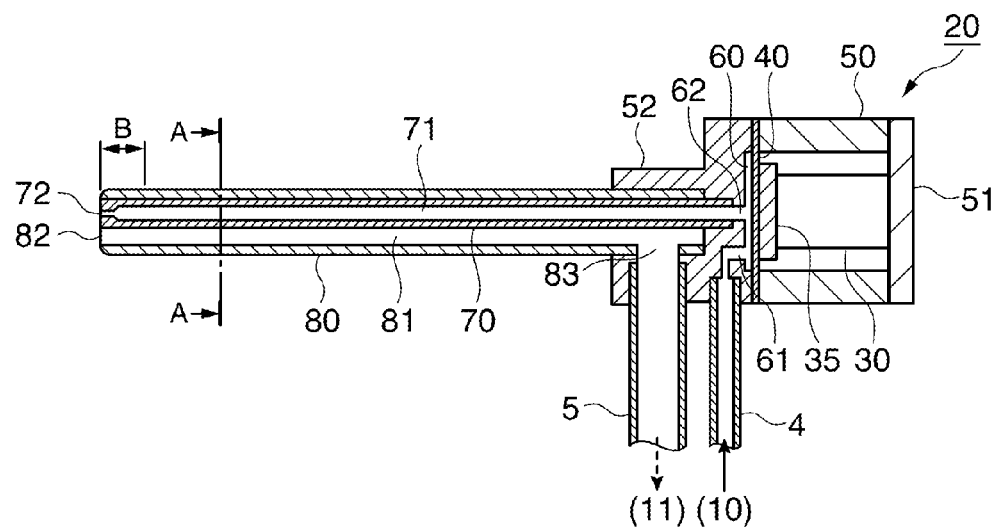
FIG. 2 is a cross-sectional view illustrating cross sections of a pulse generator, an injection pipe, and a suction pipe cut in the injection direction of fluid according to a first example.

FIG. 2 is a cross-sectional view showing cross sections of the pulse generator, the injection pipe, and the suction pipe cut in the injection direction of fluid according to the first example. The pulse generator 20 includes an inlet channel 61 through which fluid is supplied from the supply pump 10 via the fluid supply tube 4 toward the fluid chamber 60, the piezoelectric element 30 and the diaphragm 40 as the volume varying unit for varying the volume of the fluid chamber 60, and an outlet channel 62 communicating with the fluid chamber 60.

The diaphragm 40 is constituted by a disk-shaped thin metal plate and fixed by tight contact with a lower case 50 and an upper case 52. In this embodiment, the piezoelectric element 30 is a laminated-type piezoelectric element which has one end fixed to the diaphragm 40 via an upper plate 35 and the other end fixed to a bottom plate 51.

The fluid chamber 60 is a space defined by the diaphragm 40 and a concave portion formed on the surface of the upper case 52 opposed to the diaphragm 40. The outlet channel 62 opens approximately at the center of the fluid chamber 60.

The upper case 52 and the lower case 50 are combined into one body by junction of the opposed surfaces of the upper case 52 and the lower case 50 (with the diaphragm 40 interposed therebetween in the example of FIG. 2). The injection pipe 70 which has the injection channel 71 communicating with the outlet channel 62 engages with the upper case 52. The injection opening 72 having a reduced channel diameter is provided at the top end of the injection pipe 70. The injection opening 72 may be formed by a nozzle.

The suction pipe 80 as a jacket pipe for the injection pipe 70 projects from the upper case 52. An opening 83 penetrating through the side wall of the suction pipe 80 is formed in the vicinity of the root end of the suction pipe 80 close to the pulse generator 20, and the suction tube 5 is attached to the opening 83 in such a condition as to communicate with the opening 83. For an operator who holds the pulse generator 20 while performing operation, the maneuverability improves when the extending direction of the suction tube 5 in the vicinity of the pulse generator 20 is equalized with the extending direction of the fluid supply tube 4.

As illustrated in the figure, the injection pipe 70 is eccentrically inserted into the suction pipe 80. Thus, the outer circumferential surface of the injection pipe 70 and the inner circumferential surface of the suction pipe 80 contact each other, or are disposed with a small clearance left therebetween in the range of the length of the suction pipe 80. This condition is now explained with reference to FIGS. 3A and 3B.

Figure 3A:
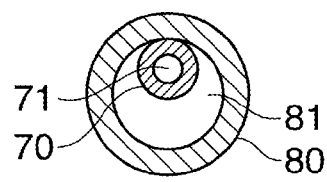
Figure 3B:
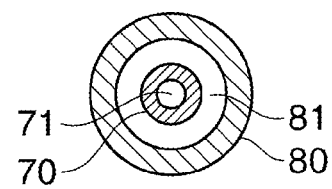

FIGS. 3A and 3B are cross-sectional views illustrating cross sections cut along an A-A line in FIG. 2. FIG. 3A shows the cross section in this example, while FIG. 3B shows the cross section in a related art. As illustrated in FIG. 3A, the outer circumferential surface of the injection pipe 70 and the inner circumferential surface of the suction pipe 80 contact each other. The clearance formed between the flow channel of the suction pipe 80 and the outer circumferential surface of the injection pipe 70 corresponds to the suction channel 81. When the flow channel diameter of the suction pipe 80 and the outside diameter of the injection pipe 70 are d1 and d2, respectively, the length (d1−d2) becomes the maximum size of the suction channel 81.

According to the technology shown in JP-A-1-313047, the injection pipe 70 is inserted concentrically with the suction pipe 80. In this case, the maximum size of the suction channel 81 becomes (d1−d2)/2. Thus, even when the total areas of the respective suction channels 81 in the structures of this example and JP-A-1-313047 are the same, the size of the suction channel 81 in the eccentric structure as in this example becomes larger than the size of the suction channel 81 in JP-A-1-313047. This relationship between the suction channels 81 in this example and in JP-A-1-313047 similarly applies to the relationship between the sizes of the suction openings 82 in both of the structures.

According to this example, the outer circumferential surface of the injection pipe 70 contacts the inner circumferential surface of the suction pipe 80. In this structure, the injection pipe 70 is inserted into the suction pipe 80 and fixed thereto by an adhesive or the like under the condition of contact between the inner circumferential surface of the suction pipe 80 and the outer circumferential surface of the injection pipe 70. Then, the suction pipe 80 and the injection pipe 70 fixed to each other are attached to the upper case 52 with press fit for assembly. In this case, as illustrated in FIG. 2, the injection pipe 70 is forced into the upper case 52 with the root end of the injection pipe 70 on the upper case 52 side projecting from the root end of the suction pipe 80, in which condition the suction pipe 80 engages with the upper case 52 with play. Then, the fitted pipes 70 and 80 are fixed to the upper case 52 by using an adhesive or the like. It is preferable that the sealing of the fixation between the upper case 52 and the injection pipe 70 and the suction pipe 80 is reinforced by using an adhesive, a solder or the like.

It is preferable that the injection pipe 70 and the suction pipe 80 are fixed to each other for the entire contacting areas of the respective pipes 70 and 80 in the length directions. However, the pipes 70 and 80 are only required to be fixed at least in the area around the top end of the injection opening 72 (a B range in FIG. 2). In this case, the injection pipe 70 and the suction pipe 80 are inserted into the upper case 52 in this order, and then the range B in the figure is fixed by bonding using an adhesive or a solder, or fixed by using a fixing method such as welding.

It is preferable that each flow channel size of the opening 83 provided on the suction pipe 80 and the suction tube 5 is made equal to or larger than the cross-sectional area of the flow channel of the suction opening 82.

The pulse flow injection operation performed by the pulse generator 20 according to this example is now explained with reference to FIGS. 1 and 2. Fluid is supplied to the inlet channel 61 at a constant pressure by the function of the supply pump 10. The fluid supply amount from the supply pump 10 is only required to be approximately the same amount as that of the pulse flow injection amount from the injection opening 72. While the piezoelectric element 30 is not actuating, fluid flows into the fluid chamber 60 by the difference between the discharging force of the supply pump 10 and the resistance of the entire flow channel of the inlet channel 61.

When the piezoelectric element 30 rapidly expands in the vertical direction with respect to the surface of the diaphragm 40 on the fluid chamber 60 side in response to a drive signal inputted to the piezoelectric element 30, the volume of the fluid chamber 60 decreases. As a result, the pressure within the fluid chamber 60 sharply increases to reach several tens atms.

In this case, the increase in the flow amount of the fluid discharged from the outlet channel 62 becomes larger than the decrease in the flow amount of the fluid flowing from the inlet channel 61 into the fluid chamber 60, thereby generating pulse flow in the injection channel 71. This pressure change produced at the time of the discharge is transmitted through the injection pipe 70 to allow injection of pulsed fluid at high speed from the injection opening 72 at the top end.

As described above, the injection pipe 70 is eccentrically inserted into the suction pipe 80 according to the first example. In this case, each size of the suction channel 81 and the suction opening 82 corresponds to the difference between the inside diameter of the suction pipe 80 and the outside diameter of the injection pipe 70. Thus, each size of the suction channel 81 and the suction opening 82 in the eccentric structure becomes larger than the corresponding size in the concentric structure. Accordingly, larger excised tissues can be sucked in the structure of the eccentrically disposed the injection pipe 70 and the suction pipe 80 than in the concentric structure. Moreover, the drainage removal amount of injected fluid increases, which provides preferable vision for surgery.

According to this example, the injection pipe 70 is fixed to the inner circumferential surface of the suction pipe 80 in the vicinity of the injection opening 72. Thus, abnormal noise generated by contact between the injection pipe 70 and the suction pipe 80 caused by vibration at the top end of the injection pipe 70 during injection of pulse flow can be prevented. Moreover, resonance of the suction pipe 80 generated by the vibration at the top end of the injection pipe 70 (injection opening) is avoided, allowing accurate injection of fluid toward the surgery portion.

While the structure which fixes the suction pipe 80 to the upper case 52 has been discussed in this example, such a structure which expands the upper case 52 such that the upper case 52 can function as a suction pipe is allowed.

The position and extending direction of the suction tube 5 are not specifically limited. However, since the operator holds the pulse generator 20 for performing operation, the system becomes well-balanced during operation and provides higher maneuverability when the suction tube 5 and the fluid supply tube 4 extend along each other in the vicinity of the pulse generator 20.

SECOND EXAMPLE

A second example is now described with reference to the drawings. While the injection pipe 70 and the suction pipe 80 are provided eccentrically for the entire lengths of the pipes 70 and 80 in the first example described above, the second example is different from the first example in that only the top end areas of the injection pipe 70 and the suction pipe are eccentrically disposed with the root end areas concentrically positioned. In the explanation of the second example, similar reference numbers are given to parts similar to the corresponding parts in the first example, and the different points between the first example and the second example are chiefly discussed.

Figure 4:
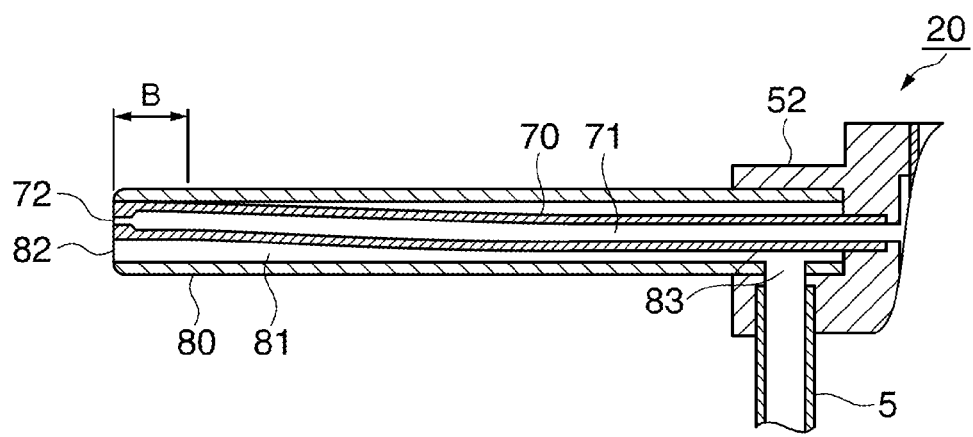
FIG. 4 is a partial cross-sectional view illustrating the structure of an injection pipe and a suction pipe according to a second example.

FIG. 4 is a partial cross-sectional view illustrating the structures of the injection pipe and the suction pipe according to the second example. The root end of the suction pipe 80 is fixed to the upper case 52 with press fit. The root end of the injection pipe 70 is fixed to the upper case 52 with press fit in such a condition as to be concentric with the suction pipe 80. The top ends (the B area in the figure) of the injection pipe 70 and the suction pipe 80 are fixed to each other by bonding such as an adhesive and a solder, or by using a fixing method such as welding.

According to this structure, the condition visually recognized on the top end side is similar to the condition shown in FIG. 3A, and the size of the suction opening 82 in this structure becomes larger than the corresponding size in the concentric structure. Thus, larger excised tissues can be sucked than in the related art which concentrically disposes the top ends of the injection pipe 70 and the suction pipe 80. Since clogging with excised tissues is easily caused at the suction opening 82, the sucking capability can be increased by widening the suction opening 82.

According to the structure which concentrically disposes the root ends of the injection pipe 70 and the suction pipe 80, the upper case 52 can be more easily processed than in the structure which fixes the eccentrically disposed pipes 70 and 80 to the upper case 52 as in the first example. Thus, the respective pipes 70 and 80 can be more easily attached to the upper case 52 with press fit.

The injection pipe 70 may be bended beforehand and urged toward the inner circumferential surface of the suction pipe 80 by the elastic force of the injection pipe 70. In this case, the suction pipe 80 is made rigid enough to resist the elastic force of the injection pipe 70 and to prevent vibration of the suction pipe 80. According to this structure, the process for fixing the top ends of the pipes 70 and 80 can be eliminated.

THIRD EXAMPLE

A third example is now described with reference to the drawings. The third example is different from the second example in that the position of connection between the suction pipe 80 and the suction tube 5 is different from the corresponding position in the second example. In the following explanation, similar reference numbers are given to parts similar to the corresponding parts in the second example, and the different points between the second example and the third example are chiefly discussed.

Figure 5:
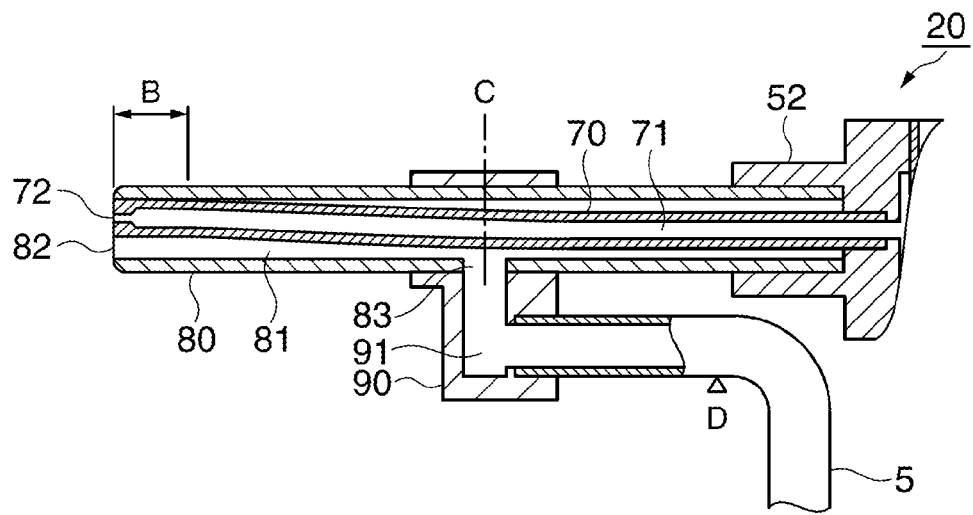
FIG. 5 is a partial cross-sectional view illustrating the structure of an injection pipe and a suction pipe according to a third example.

FIG. 5 is a partial cross-sectional view illustrating the structures of the injection pipe and the suction pipe according to the third example. The relationship between the injection pipe 70 and the suction pipe 80 is similar to that relationship in the second example. According to the second example, the top ends of the injection pipe 70 and the suction pipe 80 are eccentrically disposed and fixed to each other. Thus, the area of the suction channel 81 other than the fixed portion gradually decreases toward the root end, and becomes a channel of the same size as that size in the concentric structure in the vicinity of the opening 83 where the suction tube 5 is disposed. However, it is preferable that the opening 83 is provided in the range where the suction channel 81 is wide.

According to this example, therefore, an opening position C is disposed at a position where the suction channel 81 is relatively wide. In this structure, a tube fitting 90 having a connection channel 91 is used. The connection channel 91 is bended approximately in an L shape such that the suction tube 5 extends along the suction tube 80 and further along the fluid supply tube 4 (see FIG. 2). In this case, the suction tube 5 may be formed in the manner shown in the figure, or may be bound to the suction pipe 80 by using a binding band (not shown) around a point D in the figure when the suction tube 5 has sufficient elasticity.

According to this structure, the opening 83 is disposed at the position where the suction channel 81 becomes wider than in the concentric structure. Thus, the sucking capability does not lower. Moreover, in case of this structure, the area of the suction tube 5 around the tube fitting 90 extends along the suction pipe 80, and the area of the suction tube 5 around the pulse generator 20 extends along the fluid supply tube 4. Thus, the pulse generator 20 can be easily held, which does not deteriorate the maneuverability.

Furthermore, the structure of the upper case 52 to which the root ends of the injection pipe 70 and the suction pipe 80 are attached can be simplified.

It is possible to form the tube fitting 90 and the suction pipe 80 integrally with each other, or form the tube fitting 90 and the suction tube 5 integrally with each other.

FOURTH EXAMPLE

A fourth example according to the invention is now described with reference to the drawings. The fourth example is different from the third example in that the injection pipe 70 is bended at a position within the area between the root end and the top end to fix the top ends of the injection pipe 70 and the suction pipe 80 to each other. In the following explanation, similar reference numbers are given to parts similar to the corresponding parts in the third example, and the different points between the third example and the fourth example are chiefly discussed.

Figure 6:
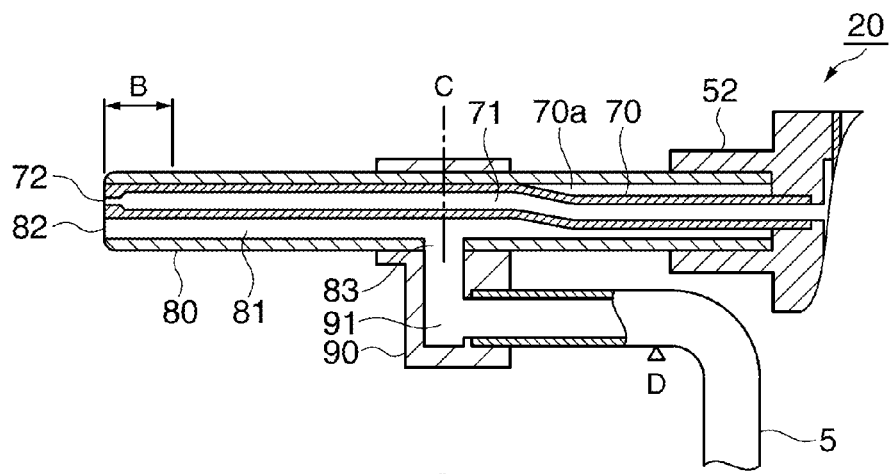
FIG. 6 is a partial cross-sectional view illustrating the structure of an injection pipe and a suction pipe according to a fourth example.

FIG. 6 is a partial cross-sectional view illustrating the structures of the injection pipe and the suction pipe according to the fourth example. The injection pipe 70 and the suction pipe 80 are attached to the upper case 52 such that the pipes 70 and 80 become concentric with each other similarly to the second example and the third example described above. According to this example, the injection pipe 70 is bended approximately at the center. The area of the injection pipe 70 between the top end and a bended portion 70a contacts the inner circumferential surface of the suction pipe 80, and is fixed thereto by bonding such as an adhesive and a solder, or by using a fixing method such as welding. The area of the injection pipe 70 between the bended portion 70a and the root end is approximately concentric with the suction pipe 80.

The opening 83 formed on the suction pipe 80 (the opening position C) is disposed at a position shifted from the bended portion 70a toward the top end and communicates with the suction tube 5 via the tube fitting 90. The suction tube 5 extends along the fluid supply tube 4.

According to this structure, the opening 83 is provided at a position within the area between the suction opening 82 and the bended portion 70a where the suction channel 81 is wide. Thus, the suction channel 81 having approximately the same size as that of the suction opening 82 can be formed, which allows larger excised tissues to be removed by suction than in the concentric structure.

When the bended portion 70a is positioned closer to the root end, the opening 83 of the suction pipe 80 can be shifted toward the pulse generator 20. In this case, the pulse generator 20 can be easily held, which improves the maneuverability. When the bended portion 70a is disposed within the area of the upper case 52, the opening 83 can be provided on the upper case 52 similarly to the structure of the second example (see FIG. 4).

FIFTH EXAMPLE

A fifth example is now described with reference to the drawings. The fifth example is different from the first example in that the suction pipe 80 linearly formed in each of the first through fourth examples is bended in the middle area. In case of an abdominal cavity surgery or the like performed by using the fluid injection device 1, there is a possibility that the surgery portion is not located on a straight line extending from the position on the body surface into which the suction pipe 80 is inserted. In this case, the top ends of the injection pipe 70 and the suction pipe 80 are required to be located at bended positions with respect to their root ends. This example is appropriate for this case. In the following explanation, similar reference numbers are given to parts similar to the corresponding parts in the second example on which the fifth example is based.

Figure 7:
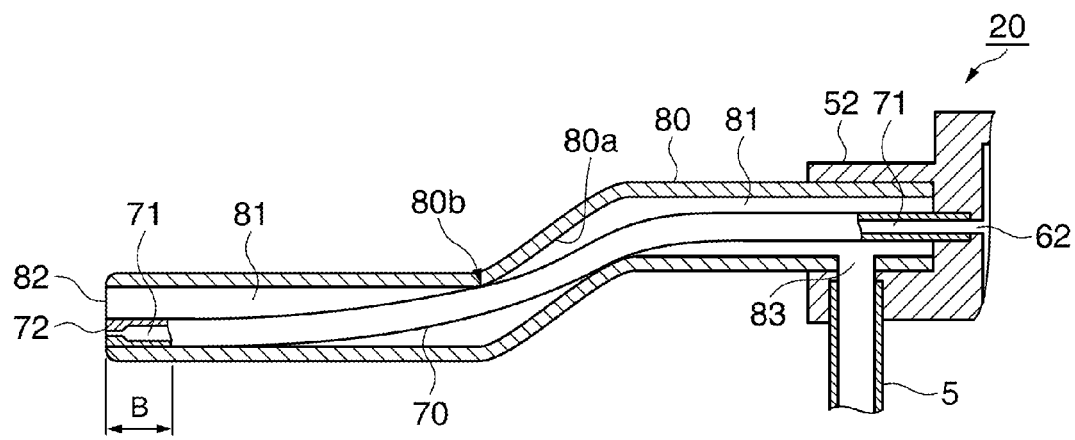
FIG. 7 is a partial cross-sectional view illustrating the structure of an injection pipe and a suction pipe according to a fifth example.

FIG. 7 is a partial cross-sectional view illustrating the structures of the injection pipe and the suction pipe according to the fifth example. The suction pipe 80 is bended at a middle position in the area between the top end and the root end. The injection pipe 70 is bended along the inner circumferential surface of the suction pipe 80, and fixed to the inner circumferential surface of the suction pipe 80 in the area around the injection opening 72 (the B range in the figure) by bonding using an adhesive, a solder or the like, or by a fixing method such as welding.

There is a method which bends the injection pipe 70 in accordance with the shape of the suction pipe 80. In practice, however, insertion of a bended tube into another bended tube is difficult from the viewpoint of structure. Thus, the substantially linear injection pipe 70 is initially fixed to the upper case 52 with press fit, and then the suction pipe 80 is inserted from the injection opening 72 side. In this case, the top end of the injection pipe 70 contacts a slope 80a at the bending position of the suction pipe 80, and then is bended in accordance with the shapes of the slide 80a and a bended portion 80b with to obtain a shape shown in FIG. 7 when the root end of the suction pipe 80 reaches the upper case 52. In case of the abdominal cavity surgery, each length of the injection pipe 70 and the suction pipe 80 is approximately in the range from 200 m to 400 mm. Thus, the actual bending angle becomes a gentler angle than the angle in the condition shown in the figure.

According to this example, therefore, the top ends of the injection pipe 70 and the suction pipe 80 can be eccentrically disposed even when the top ends of the injection pipe 70 and the suction pipe 80 are located at bended positions with respect to their root ends in correspondence with the surgery portion or the surgery method. Thus, the suction opening 82 in this structure becomes wider than in the concentric structure. In this example, the bended portion of the suction channel 81 has an area smaller than the suction opening 82. However, since the outer shape of the injection pipe 70 is circular, the resistance of the flow channel is small enough to avoid lowering of the capability of sacking the excised tissues.

According to this example, the injection pipe 70 is inserted along the inner circumferential surface of the bended suction pipe 80. Thus, the top end of the injection pipe 70 is urged toward the inner circumferential surface of the suction pipe 80 by the elastic force of the injection pipe 70. Accordingly, the top end of the injection pipe 70 is not required to be fixed as long as the urging force is large enough to prevent vibration. Considering this point, the rigidity of the suction pipe 80 is made larger than the rigidity of the injection pipe 70.

SIXTH EXAMPLE

A sixth example is now described with reference to the drawings. The sixth example is different from the first through fifth examples in that the fluid injection direction which extends on a straight line drawn from the injection channel 71 or in parallel with the injection channel 71 in each of the first through fifth examples is inclined to the injection channel 71. There is a case in which excision is performed at a position shifted from the extending direction of the suction pipe 80 depending on the surgery portion. This example is appropriate for this case. In the following explanation, similar reference numbers are given to parts similar to the corresponding parts in the first example on which the sixth example is based.

Figure 8:
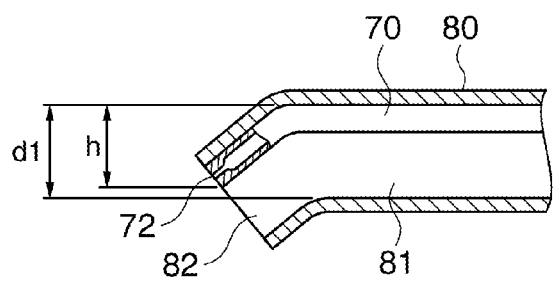
FIG. 8 is a partial cross-sectional view illustrating the structure of an injection pipe and a suction pipe according to a sixth example.

FIG. 8 is a partial cross-sectional view illustrating the structures of the injection pipe and the suction pipe. The top ends of the injection pipe 70 and the suction pipe 80 are bended, and the injection pipe 70 follows the inner circumferential surface of the bended portion of the suction pipe 80. The area of the injection pipe 70 around the injection opening 72 is fixed to the inner circumferential surface of the suction pipe 80 by using an adhesive, a solder or the like, or by a fixing method such as welding.

When the flow channel diameter of the suction pipe 80 and the bending height of the injection pipe 70 are d1 and h, respectively, the flow channel diameter d1 is determined such that the relationship h<d1 holds. This arrangement allows insertion of the injection pipe 70 into the suction pipe 80.

According to this structure, excision and removal of excised tissues by suction at a position shifted from the extending direction of the suction pipe 80 can be achieved in accordance with the surgery portion.

The structure in this example maybe applied to each structure of the first through fifth examples.

SEVENTH EXAMPLE

A seventh example is now described with reference to the drawings. Since the injection opening 72 is disposed eccentrically to the suction opening 82 as described in each of the examples, it is difficult for the operator to directly recognize the injection opening 72 by visual check. For overcoming this drawback, a feature of the seventh example resides in that a mark representing the position of the injection opening 72 is provided in the vicinity of the suction opening 82.

FIGS. 9A and 9B illustrate the top ends of the injection pipe and the suction pipe according to the seventh example. FIG. 9A is a cross-sectional view, and FIG. 9B is a front view as viewed from the top end (in the direction indicated by an arrow E). As illustrated in FIGS. 9A and 9B, a notch 73 as a mark is formed on the suction pipe 80 in the vicinity of the injection opening 72. The notch 73 is formed in such a position and a shape as to overlap with the periphery of the suction opening 82. Thus, the operator can visually recognize the top end of the injection pipe 70 (injection opening position).

The mark may be a notch as shown in the figure, or other marks such as a seal, a small hole, and a paint provided on the outer circumferential surface of the suction pipe 80. When the mark is the notch 73 as in this example, the operator can directly recognize the position of the injection opening 72 by visual check during operation. Thus, the operator can inject fluid to the accurate surgery portion for excision.

EIGHTH EXAMPLE

An eighth example is now described with reference to the drawings. While the one notch 73 is provided as a mark in the seventh example, the eighth example is different in that the mark is constituted by notches formed in such positions as to overlap with the suction opening or through holes opened in the vicinity of the suction opening.

FIG. 10 is a front view illustrating the top end of the suction pipe according to the eighth example. As illustrated in FIG. 10, four notches 73a, 73b, 73c, and 73d are formed on the top end of the suction pipe 80 in such positions as to overlap with the periphery of the suction opening 82. According to the example shown in FIG. 10, the notch 73a corresponds to a mark indicating the position of the injection opening 72. The other notches 73b through 73d are provided to supplement the sucking function of the suction opening 82. Thus, the notch 73a has a position and shape appropriate for a mark, while the other notches 73b through 73d have positions and shapes allowing suction of excised tissues. The notches 73a through 73d may be through holes (not shown) penetrating the side surface of the top end of the suction pipe 80.

Accordingly, the mark indicating the position of the injection opening 72 can be provided in the vicinity of the suction opening 82 by formation of the notches 73a through 73d. These notches 73a through 73d can further supplement the size of the suction opening 82, and thus can increase the capability of sucking excised tissues.

Furthermore, the through holes formed in the vicinity of the suction opening 82 can remove excised tissues existing on the side surface of the top end by suction.

What is claimed is:
1. A fluid injection device comprising:
a pulse generator which converts fluid into pulse flow;
an injection pipe having an injection opening communicating with the pulse generator;

a suction pipe, wherein the injection pipe is entirely inserted into the suction pipe, the outer circumferential surface of the injection pipe contacting the inner circumferential surface of the suction pipe; and a suction channel and a suction opening formed between the inner circumferential surface of the suction pipe and the outer circumferential surface of the injection pipe, wherein the injection pipe is eccentric to the suction pipe where the injection pipe contacts the suction pipe.

2. The fluid injection device according to claim 1, wherein a mark indicating the position of the injection opening is provided on the suction pipe in the vicinity of the suction opening.

3. The fluid injection device according to claim 2, wherein the mark is a notch formed in such a position as to overlap with the periphery of the suction opening, or a through hole opened in the vicinity of the suction opening.

4. The fluid ejection device according to claim 1, wherein a top end of the injection pipe protrudes from a top end of the suction pipe.

* * * * *